United States Patent [19]

Barone

[11] Patent Number: 4,680,122
[45] Date of Patent: Jul. 14, 1987

[54] ULTRAFILTRATION CONTROL FOR HEMODIALYSIS

[75] Inventor: David Barone, Oklahoma City, Okla.

[73] Assignee: Organon Teknika Corporation, Oklahoma City, Okla.

[21] Appl. No.: 534,034

[22] Filed: Sep. 10, 1983

[51] Int. Cl.⁴ .............................................. B01D 13/00
[52] U.S. Cl. ..................................... 210/637; 210/646; 210/648; 210/321.3; 210/929
[58] Field of Search ................. 210/741, 929, 90, 637, 210/85, 646, 87, 648, 34.2, 34.3

[56] References Cited

U.S. PATENT DOCUMENTS

| | | | |
|---|---|---|---|
| 3,669,880 | 6/1972 | Marantz et al. | 210/929 X |
| 4,113,614 | 9/1978 | Rollo et al. | 210/90 X |
| 4,132,644 | 1/1979 | Kolberg | 210/929 X |
| 4,334,988 | 6/1982 | Milligan | 210/929 X |
| 4,370,983 | 2/1983 | Lichtenstein | 210/929 X |
| 4,381,999 | 5/1983 | Boucher et al. | 210/741 X |
| 4,486,303 | 12/1984 | Brous | 210/87 |

Primary Examiner—Frank Spear
Attorney, Agent, or Firm—William M. Blackstone

[57] ABSTRACT

There is provided an improved system for controlling ultrafiltration in hemodialysis which is independent of the membrane used in the dialyzer. A load cell measures the instantaneous amounts of fluid in a reservoir which receives fluids from the dialyzer and feeds this information into an electronic controller which has been programmed for the desired ultrafiltration. The controller generates an error signal and controls a negative pressure control valve which, in turn, determines the rate and thus amount of ultrafiltration.

7 Claims, 2 Drawing Figures

ULTRAFILTRATION CONTROL FOR HEMODIALYSIS

BACKGROUND OF THE INVENTION

This invention relates to a system for controlling ultrafiltration in hemodialysis. More particularly, it relates to the control of ultrafiltration in a closed hemodialysis system.

Hemodialysis is a technique of removing certain toxic wastes from the human body in cases of renal failure by the use of an artificial kidney in conjunction with an associated machine. The patient's blood is temporarily brought outside of the body by tubes and permitted to pass by at least one semipermeable membrane, which may be a group of hollow fibers, in the artificial kidney, also called a dialyzer. The semipermeable membrane separates the blood from dialysate solution. The impurities from the blood pass through the membrane and into the dialysate solutions primarily by osmotic pressures. The cleansed blood is then returned to the body. During this procedure it is also necessary to remove excess fluids from the body. This is accomplished by a technique known as ultrafiltration. The amount of ultrafiltrate which is removed from the body is normally controlled by pressure across the semipermeable membrane. This transmembrane pressure is the result of the differential between the blood pressure and the pressure which exists on the dialysate side of the membrane. A description of an ultrafiltration system in a closed dialysis system is set forth in U.S. Pat. No. 3,669,880 assigned to the assignee of the present invention and which is hereby incorporated by reference.

One of the problems associated with prior art ultrafiltration control systems has been a lack of accuracy because of the differing characteristics of each dialyser which is used for each dialysis treatment. In particularly, the rate of passage of ultrafiltrate through the semipermeable membrane will differ for dialyzers from different manufacturers as well as those of the same manufacturer. Applicant has overcome this problem of inaccuracy with the present invention.

In general there are two types of hemodialysis systems. One type is referred to as a single pass system whereby the dialysate solution passes through the dialysate compartment of the dialyzer only once and then is discharged as waste. The single pass system obviously requires a great deal of fluid to fully treat the patient. A second type of system, and the system which is referred to in the previously mentioned U.S. Pat. No. 3,669,880, is a closed system. The closed system may utilize a filter such as an ion exchanger, for example, a zirconium phosphate column together with charcoal and other materials, to regenerate the used dialysate solution and pass the regenerated solution across the membrane over and over again until the treatment has been completed. While the system of the present invention has been specifically designed for use in a closed system, with minor modification it could be utilized in a single pass system.

OBJECTS OF THE INVENTION

It is therefore one object of this invention to provide an improved ultrafiltration control for hemodialysis systems.

It is another object to provide a highly accurate ultrafiltration control system which is independent from the particular dialyzer which is utilized.

It is still another object to provide an ultrafiltration system for a closed hemodialysis system.

SUMMARY OF THE INVENTION

In accordance with one form of this invention there is provided a method and apparatus for controlling ultrafiltration in hemodialysis. A dialyzer is provided having a blood compartment and a dialysate compartment. A semipermeable membrane separates the blood compartment from the dialysate compartment. A dialysate fluid conduit is connected to the dialysate compartment and a dialysate fluid reservoir is further connected to the conduit. A mechanism is provided for measuring the quantity of fluid in the reservoir at predetermined time intervals to determine the amount of ultrafiltrate from the blood compartment through the membrane to the dialysate compartment. A further mechanism is provided for comparing the measured ultrafiltration to a desired ultrafiltration. A means is provided for controlling the pressure across the membrane in response to the comparison of the measured ultrafiltration to the desired amount so that the rate and thus actual amount of ultrafiltration is ultimately controlled.

BRIEF DESCRIPTION OF THE DRAWINGS

The subject matter which is regarded as the invention is set forth in the appended claims. The invention itself however, together with further objects and advantages thereof may be better understood by referring to the following description taken in conjunction with the accompanying drawings in which:

DESCRIPTION OF THE PREFERRED EMBODIMENT

Figure 1:
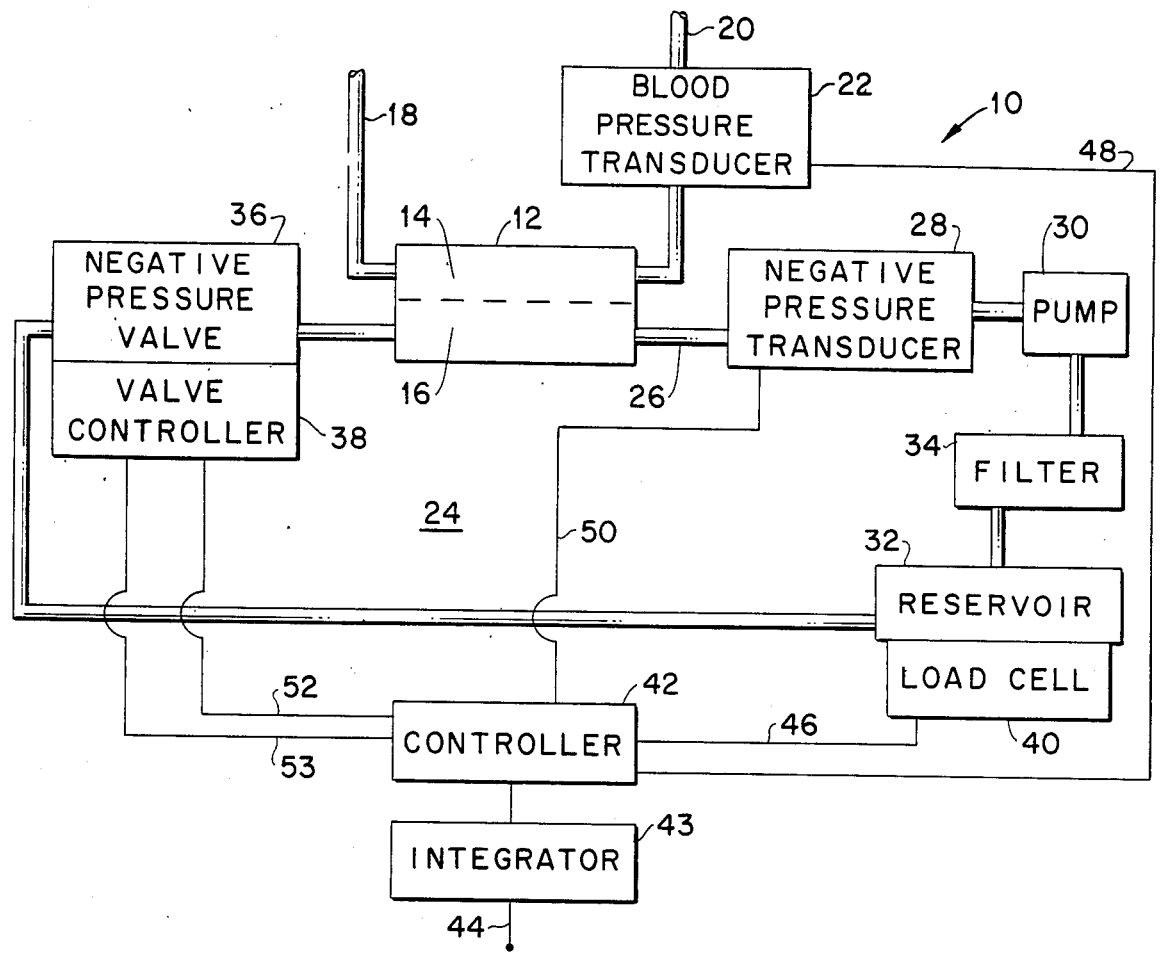
FIG. 1 is a block diagram of the ultrafiltration control system of the subject invention.

Referring now more particularly to FIG. 1, there is provided closed loop hemodialysis system 10 which utilizes artificial kidney or dialyzer 12. Dialyzer 12 is divided into blood compartment 14 and dialysate compartment 16. Normally the blood compartment of the dialyzer will include a plurality of hollow fiber semipermeable membranes 13. One such dialyzer is the Nephross disposable dialyzer commercially available from Organon Teknika Corporation of Oklahoma City, Okla.

Blood chamber 14 is connected to the patient's blood vessels through tubes 18 and 20. A blood pressure transducer 22 is connected to blood tube 20. The dialysate loop 24 is shown in simplified form in FIG. 1 in that some of the apparatus normally in the loop is not necessary in the description of the subject invention. A more detailed description of the dialysate loop is set forth in U.S. Pat. No. 3,669,880, which has been previously been incorporated herein by reference.

Dialysate loop 24 includes dialysate chamber 16 of artificial kidney 12. Dialysate fluid conduit 26 forms the tubing for the loop and extends from one side of the dialysate chamber 16 to the other. Negative pressure sensor 28 is connected to the conduit 26 and measures the fluid pressure within dialysate compartment 16. Pump 30 is further connected in series with the dialysate loop 24 for circulating the dialysate fluid about the loop. Fluid reservoir 32 is connected to pump 30, through filter 34, and contains an adjustable amount of dialysate fluid. Filter 34 removes impurities from the dialysate fluid which the fluid has picked up in chamber 16. Normally filter 34 includes an ion exchange column such as a zirconium phosphate layer, a layer of urease, together with a charcoal layer. Filter 34 is normally disposable and is changed for each dialysis treatment, just as artificial kidney 12.

Negative pressure valve 36 is also connected in the dialysate loop 24 for controlling the pressure within dialysate chamber 16. Valve controller 38 is connected to negative pressure valve 36 for controlling the opening and constricting of the negative pressure valve. Load cell 40 is coupled to reservoir 32 for measuring the instantaneous amount of fluid in reservoir 32. Electronic controller 42 is electrically connected to load cell 40, blood pressure transducer 22, negative pressure sensor 28 and valve controller 38, and integrator 43 having input terminal 44. Electronic controller 42 receives signal information from load cell 40, blood pressure transducer 22 and negative pressure sensor 28 over lines 46, 48 and 50, respectively, the signals being amplified within the controller. Electronic contoller 42 controls the valve controller 38 through lines 52 and 53. Electronic controller 42 includes a microprocessor which functions, inter alia, as a comparator.

Figure 2:
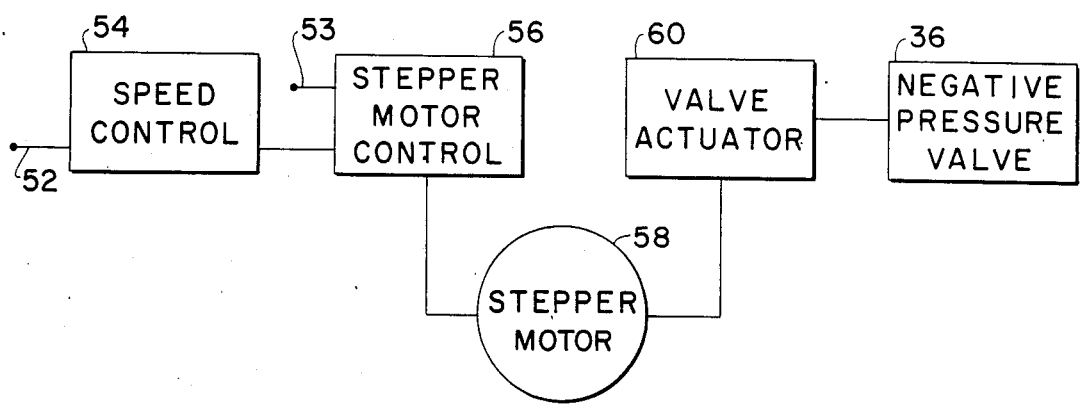
FIG. 2 is a block diagram of the negative pressure control system utilized in FIG. 1.

FIG. 2 shows a block diagram of valve controller 38. Input terminal 52, from controller 42 in FIG. 1, is connected to speed control 54 which, in turn, is connected to stepper motor control 56. Input terminal 53 from controller 42 is also connected to stepper motor control for providing a directional signal. Stepper motor 58 is connected to the stepper motor control 56 and to valve actuator 60. The actuator 60 controls the movement of negative pressure value 36.

The above-described system operates to control the ultrafiltration rate as follows. For each treatment of a patient, a new artificial kidney is utilized having a slightly different membrane ultrafiltration index, which is normally measured in liters per hour per unit of pressure (normally measured in millimeters of mercury). Reservoir 32 is partially filled with dialysate solution. The blood vessels of the patient are then connected to blood tubes 18 and 20. The user inputs the desired ultrafiltration rate into integrater 43 at input terminal 44, which electronically integrates the inputted rate over a period of time to come up with the desired or target amount of ultrafiltration. Pump 30 causes the flow of dialysate around loop 24 through conduit 26. A second pump, not shown, may be connected to either blood line 18 or blood line 20 for causing the patient's blood to be circulated through blood chamber 14 in dialyzer 12. The clean dialysate solution passes into dialysate chamber 16, thereby picking up impurities from the blood primarily through osmotic pressure across the membrane 13. The impurity ladened dialysate passes through filter 34, and dialysate is cleansed and then again passed through chamber 16. The negative pressure valve 36 controls the transmembrane pressure and this pressure is sensed by negative pressure sensor 28 and blood pressure transducer 22.

Ultrafiltration begins when pump 30 operates in that there is always a pressure across membrane 13 in the direction of dialysate compartment 16. Excess fluid begins to accumulate in reservoir 32 and its weight is measured by load cell 40. The load cell weight information is sampled by controller 42 at predetermined times. Simultaneously the controller is sampling the negative pressure sensor 28 and the blood pressure transducer 22 to determine the instantaneous value of transmembrane pressure. If the membrane ultrafiltration index were known, that is, if all artificial kidneys had the identical membrane characteristics, the ultrafiltration rate would be determined as follows:

$$UFT = K \times TMP$$

where
UFR=ultrafiltration rate (liters/hour)
K=membrane ultrafiltration index (liters/hour/mmHg)
TMP=transmembrane presure (mmHg)

However, since membrane ultrafiltration index, K, varies for various dialyzers, the system of the subject invention solves the problem by sampling the changes in load cell reading over small units of time. The contoller 42 performs the following calculations:

$$E(t) = TUF_o(t) - TUF(t)$$

Where:
$TUF_o(t)$=momentary value of the "target" total ultrafiltration removed
$TUF(t)$=momentary value of the "actual" total ultrafiltration removed
$E(t)$=momentary value of the difference between the two above (the "error") in units of ml.

$$TMP(t+\Delta t) = TMP(t) + E(t) \times \beta$$

Where:
$TMP(t)$=current transmembrane pressure
$TMP(t+\Delta t)$=transmembrane pressure to be adjusted in the next time frame ($\Delta t$)
$\beta$=error amplifier gain (constant)

$$TMP(t) = PB(t) + PD(t)$$

Where:
$PB(t)$=blood compartment pressure as measured by the blood pressure transducer
$PD(t)$=dialysate compartment pressure as measured by negative pressure transducer.

$$TMP(t + \Delta t) = PB(t + \Delta t) + PD(t + \Delta t)$$

$$PB(t + \Delta t) + PD(t + \Delta t) = PB(t) + PD(t) + E(t) \times \beta$$

$$PD(t + \Delta t) = PB(t) + PD(t) - PB(t + \Delta t) + E(t) \times \beta$$

Since the blood pressure changes very slowly during this period $\Delta T$, it may be assumed that $PB(t) = PB(t+\Delta t)$, thus $PB(t+\Delta t) = PD(t) + E(t) \times \beta$. The dialysate pressure, $PD(P+\Delta t)$ is controlled by the opening and closing of the negative pressure valve 36. Valve controller 36 includes a stepper motor 58 which is responsive to the stepper motor control 56 which, in turn, is responsive to speed control 54 for rotational speed, and terminal 53 for direction. The stepper motor rotation controls valve actuator 62 which, in turn, controls the opening and closing of negative pressure valve 36. Thus the ultrafiltration rate is controlled by determining the difference between the actual measured ultrafiltration amount removed and the target amount which has been inputted to controller 42. Most prior art ultrafiltration controllers are based on differential measurement of flow, an error in the measurement of flow or in the ultrafiltration rate which will be accummulated and, as a result, be reflected as a relatively large error in the final determination of the total ultrafiltration removed. The above-described system results in more accurate ultrafiltration as the error depends only on the accuracy of the load cell 40.

The system described aboved has been constructed and operated using the following components available from the below listed sources:

| Components | Sources: |
| --- | --- |
| Dialyzer 12 | Organon Tekinka Corporation |
| Blood Pressure Transducer 22 | Micro-Switch Company |
| Negative Pressure Sensor 28 | Micro-Switch Company |
| Pump 30 | Micro-Pump Company |
| Load Cell 40 | TEDEA Company |
| Controller 42 | Rockwell 6502 |
| Filter 34 | Organon Teknika Corporation |
| Stepper Motor 58 | Airpax Company |

Integrater 43, negative pressure valve 36, speed control 54, stepper motor control 56 and valve actuator 60 are readily built from standard off-the-shelf electrical and mechanical devices, and all are well known to those skilled in the art.

From the foregoing description of the preferred embodiment of the invention it will be apparent that many modifications may be made therein. It will be understood that this embodiment of the invention is intended as an exemplification of the invention only and the invention is not limited thereto. For example, with very minor changes the system could be adapted for a single pass operation. It is understood, therefore, that it is intended in the appended claims to cover all such modifications which fall within the true spirit and scope of the invention.

I claim:

1. A process for automatically controlling ultrafiltration in a closed dialysis system during hemodialysis comprising the steps of:

causing the flow of blood on one side of a semipermeable membrane, causing the flow of dialysate solution on the other side of said semipermeable membrane; collecting dialysate fluid and ultrafiltrate fluid in a reservoir; measuring the transmembrane pressure; indicating a desired ultrafiltration rate; measuring the total quantity of dialysate fluid and ultrafiltrate fluid in the reservoir at predetermined time intervals; comparing the actual quantity of fluid in the reservoir for each of said time intervals to the required quantity for the desired ultrafiltration rate; calculating the error between the required and the actual quantity of fluid in the reservoir; and adjusting the transmembrane pressure in response to the error for each of said time intervals.

2. The process of claim 1, wherein the pressure across said semipermeable membrane is adjusted using a negative pressure valve.

3. The process of claim 2, wherein a stepper motor is used for adjusting said negative pressure valve.

4. The process of claim 1, wherein the quantity of fluid in said reservoir is measured using a load cell connected to said reservoir.

5. The process of claim 1, wherein the actual quantity of fluid is compared to the quantity for the desired ultrafiltration rate using a microprocessor.

6. A process as set forth in claim 1, further including the step of recirculating said dialysate solution past said semipermeable membrane a plurality of times.

7. A process as set forth in claim 6, further including the step of cleansing said dialysate solution prior to each recirculation.

* * * * *